United States Patent
Lassila et al.

(10) Patent No.: US 6,455,234 B1
(45) Date of Patent: Sep. 24, 2002

(54) ACETYLENIC DIOL ETHYLENE OXIDE/PROPYLENE OXIDE ADDUCTS AND THEIR USE IN PHOTORESIST DEVELOPERS

(75) Inventors: Kevin Rodney Lassila, Macungie; Paula Ann Uhrin, Allentown; Joel Schwartz, Lansdale, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/024,893

(22) Filed: Dec. 18, 2001

Related U.S. Application Data

(63) Continuation-in-part of application No. 09/477,600, filed on Jan. 4, 2000, now abandoned, which is a continuation-in-part of application No. 09/304,607, filed on May 4, 1999, now Pat. No. 6,313,182, which is a continuation-in-part of application No. 09/304,612, filed on May 4, 1999, now abandoned.

(51) Int. Cl.$^7$ .............. G03F 7/32; C07C 43/11; C07C 43/18; C11D 17/00; C11D 17/08
(52) U.S. Cl. .............. 430/325; 430/311; 430/331; 510/178; 510/421; 568/616
(58) Field of Search ................ 430/331, 329, 430/311, 325; 510/178, 421; 568/616

(56) References Cited

U.S. PATENT DOCUMENTS

| | | | |
|---|---|---|---|
| 2,106,180 A | 1/1938 | Kreimeier et al. | |
| 2,163,720 A | 6/1939 | Vaughn et al. | |
| 2,250,445 A | 7/1941 | Bruson et al. | |
| 3,268,593 A | 8/1966 | Carpenter | 260/615 |
| 4,117,249 A | 9/1978 | De Simone et al. | 568/855 |
| 4,374,920 A | 2/1983 | Wanat et al. | 430/331 |
| 4,833,067 A | 5/1989 | Tanaka et al. | 430/331 |
| 5,069,996 A | 12/1991 | Rogler | 430/168 |
| 5,098,478 A | 3/1992 | Krishnan et al. | 106/23 |
| 5,562,762 A | 10/1996 | Mrvos et al. | 106/22 |
| 5,650,543 A | 7/1997 | Medina | 568/616 |
| 5,747,224 A | 5/1998 | Sato et al. | 430/331 |
| 5,753,421 A | 5/1998 | Sato et al. | 430/325 |
| 5,756,267 A | 5/1998 | Matsuda et al. | 430/331 |
| 5,922,522 A | 7/1999 | Barr et al. | 430/493 |
| 6,261,745 B1 * | 7/2001 | Tanabe et al. | 430/331 |

FOREIGN PATENT DOCUMENTS

| | | |
|---|---|---|
| JP | 06279081 | 3/1996 |
| JP | 04071894 | 8/1996 |
| JP | 04091168 | 3/1997 |
| JP | 2621662 | 4/1997 |
| JP | 2636954 | 4/1997 |
| JP | 03063187 | 12/1997 |
| JP | 09150577 | 10/1998 |
| JP | 10319606 | 12/1998 |

OTHER PUBLICATIONS

Schwartz, J. "The Importance of Low Dynamic Surface Tension in Waterborne Coatings," Journal of Coatings Technology, Sep. 1992.

Wirth, W.; Storp, S.; Jacobsen, W., "Mechanisms Controlling Leaf Retention of Argicultural Spray Solutions" Pestic. Sci. 1991, 33, 411–420.

Medina, S. W.; Sutovich, M. N., "Using Surfactants to Formulate VOC Compliant Waterbased Inks," Am Ink Maker 1994, 72 (2), 32–38.

"Microlithography, Science and Technology" edited by J. R. Sheats and B. W. Smith, Marcel Dekker, Inc. 1998, pp 551–553.

Leeds et al. I & EC Product Research and Development 1965, 4, 237.

* cited by examiner

Primary Examiner—Richard L. Schilling
(74) Attorney, Agent, or Firm—Michael Leach

(57) ABSTRACT

This invention provides water-based compositions, particularly coating, ink, fountain solution and agricultural compositions, manifesting reduced equilibrium and dynamic surface tension by the incorporation of a surface tension reducing amount of an acetylenic diol ethylene oxide/propylene oxide adduct of the structure

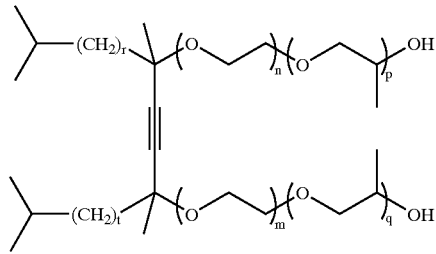

where r and t are 1 or 2, (n+m) is 1 to 30 and (p+q) is 1 to 30. Use of such adducts as surfactants in photoresist developer/electronics cleaning compositions is particularly advantageous.

Also disclosed is a method for making random and block EO/PO adducts of acetylenic diols by reacting an acetylenic diol with EO and/or PO in the presence of a trialkylamine or Lewis acid.

20 Claims, No Drawings

ACETYLENIC DIOL ETHYLENE OXIDE/PROPYLENE OXIDE ADDUCTS AND THEIR USE IN PHOTORESIST DEVELOPERS

RELATED U.S. APPLICATION DATA

This application is a continuation-in-part of U.S. patent application Ser. No. 09/477,600 filed Jan. 4, 2000, now abandoned, which is a continuation-in-part of U.S. patent applications Ser. No. 09/304,607, now U.S. Pat. No. 6,313,182, and Ser. No. 09/304,612, now abandoned both filed May 4, 1999, all of which are hereby incorporated by reference.

BACKGROUND OF THE INVENTION

The invention relates to acetylenic diol alkylene oxide adducts, their manufacture and their use to reduce the surface tension in water-based systems. In another aspect it relates to the use of such adducts as a wetting agent in aqueous photoresist developers.

The ability to reduce the surface tension of water is of great importance in waterborne coatings, inks, adhesives, and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important when the system is at rest. However, the ability to reduce surface tension under dynamic conditions is of great importance in applications where high surface creation rates are utilized. Such applications include spraying, rolling and brushing of coatings or spraying of agricultural formulations, or high-speed gravure or ink-jet printing. Dynamic surface tension is a fundamental quantity which provides a measure of the ability of a surfactant to reduce surface tension and provide wetting under such high-speed application conditions.

Traditional nonionic surfactants such as alkylphenol or alcohol ethoxylates, and ethylene oxide (EO)/propylene oxide (PO) copolymers have excellent equilibrium surface tension performance but are generally characterized as having poor dynamic surface tension reduction. In contrast, certain anionic surfactants such as sodium dialkyl sulfosuccinates can provide good dynamic results, but these are very foamy and impart water sensitivity to the finished coating.

Surfactants based on acetylenic glycols such as 2,4,7,9-tetramethyl-5-decyne-4,7-diol and its ethoxylates are known for their good balance of equilibrium and dynamic surface-tension-reducing capabilities with few of the negative features of traditional nonionic and anionic surfactants.

For many applications it would be desirable to produce acetylenic diol derivatives which have alternative properties. For example, in applications in which excellent dynamic performance is required, it is often desirable to have a surfactant which has higher critical aggregation concentration (solubility limit or critical micelle concentration) because higher bulk surfactant concentrations lead to a higher diffusive flux of surfactant to newly created surface, and consequently lower dynamic surface tension. Traditionally, acetylenic diol surfactants with higher water solubility have been obtained by reaction of the parent with ethylene oxide; greater degrees of ethoxylation provide greater water solubility. Unfortunately, increasing the level of ethoxylation also introduces a tendency to foam, introducing inefficiencies during formulation, defects during application, and process issues in other applications. The problem of foaming is particularly troublesome in photoresist developers used in semiconductor fabrication.

The demands of semiconductor manufacture have required the use of high performance surfactants and wetting agents in photoresist developer formulations. As line features shrink to smaller sizes and photoresist substrate materials become more aliphatic in nature (i.e. having lower surface energy), aqueous developer solutions are being formulated with surface tension reducing agents. Another requirement for these developers is that they have a low tendency to foam. This is accentuated by the movement toward larger wafer sizes. Low foam formation is particularly important when using spray-puddle techniques because microbubble entrainment during spreading of the solution over the photoresist surface can lead to defects. Surfactants that have been used in the past to increase wetting of the photoresist typically lead to higher foam formation. For the most part the industry has focused on the effect of surfactant on photoresist performance, such as contrast, critical dimension, and feature sharpness. Although the cleaning ability of underlying substrates is enhanced by typical surfactants, foam formation still remains a problem.

Low dynamic surface tension is of great importance in the application of waterborne coatings. In an article, Schwartz, J. "The Importance of Low Dynamic Surface Tension in Waterborne Coatings", Journal of Coatings Technology, September 1992, there is a discussion of surface tension properties in waterborne coatings and a discussion of dynamic surface tension in such coatings. Equilibrium and dynamic surface tension were evaluated for several surface-active agents. It is pointed out that low dynamic surface tension is an important factor in achieving superior film formation in waterborne coatings. Dynamic coating application methods require surfactants with low dynamic surface tensions in order to prevent defects such as retraction, craters, and foam.

Efficient application of agricultural products is also highly dependent on the dynamic surface tension properties of the formulation. In an article, Wirth, W.; Storp, S.; Jacobsen, W. "Mechanisms Controlling Leaf Retention of Agricultural Spray Solutions"; Pestic. Sci. 1991, 33, 411–420, the relationship between the dynamic surface tension of agricultural formulations and the ability of these formulations to be retained on a leaf was studied. These workers observed a good correlation between retention values and dynamic surface tension, with more effective retention of formulations exhibiting low dynamic surface tension.

Low dynamic surface tension is also important in high-speed printing as discussed in the article "Using Suffactants to Formulate VOC Compliant Waterbased Inks", Medina, S. W.; Sutovich, M. N. Am. Ink Maker 1994, 72 (2), 32–38. In this article, it is stated that equilibrium surface tensions (ESTs) are pertinent only to ink systems at rest. EST values, however, are not good indicators of performance in the dynamic, high speed printing environment under which the ink is used. Dynamic surface tension is a more appropriate property. This dynamic measurement is an indicator of the ability of the surfactant to migrate to a newly created ink/substrate interface to provide wetting during high-speed printing.

Tetramethylammonium hydroxide (TMAH) is the chemical of choice in aqueous alkaline solutions for developing photoresists according to Microlithography, Science and Technology, edited by J. R. Sheats and B. W. Smith, Marcel Dekker, Inc., 1998, pp 551–553. Surfactants are added to the aqueous TMAH solutions to reduce development time and scumming and to improve surface wetting.

U.S. Pat. No. 5,098,478 discloses water-based ink compositions comprising water, a pigment, a nonionic surfactant and a solubilizing agent for the nonionic surfactant. Dynamic surface tension in ink compositions for publication gravure printing must be reduced to a level of about 25 to 40 dynes/cm to assure that printability problems will not be encountered.

U.S. Pat. No. 5,562,762 discloses an aqueous jet ink of water, dissolved dyes and a tertiary amine having two polyethoxylate substituents and that low dynamic surface tension is important in ink jet printing.

In applications which require good dynamic performance and low foaming, acetylenic glycol-based surfactants have become industry standards. The following patents and articles describe various acetylenic alcohols and their ethoxylates as surface-active agents:

U.S. Pat. No. 3,268,593 and Leeds, et al, *I&EC* Product Research and Development 1965, 4,237, disclose ethylene oxide adducts of tertiary acetylenic alcohols represented by the structural formula

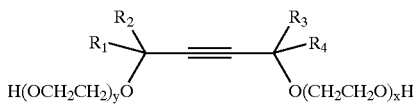

wherein $R_1$ and $R_4$ are alkyl radicals having from 3–10 carbon atoms and $R_2$ and $R_3$ are methyl or ethyl and x and y have a sum in the range of 3 to 60, inclusive. Specific ethylene oxide adducts include the ethylene oxide adducts of 3-methyl-1-nonyn-3-ol, 7,10-dimethyl-8-hexadecyne-7,10-diol; 2,4,7,9-tetramethyl-5-decyne-4,7-diol and 4,7-dimethyl-5-decyne-4,7-diol. Preferably, the ethylene oxide adducts range from 3 to 20 units. Also disclosed is a process for the manufacture of materials of this type using trialkylamine catalysts.

U.S. Pat. No. 4,117,249 discloses 3 to 30 mole ethylene oxide (EO) adducts of acetylenic glycols represented by the structural formula

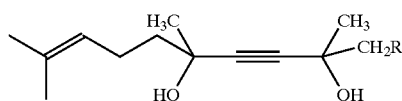

wherein R is hydrogen or an alkenyl radical. The acetylenic glycols are acknowledged as having utility as surface-active agents, dispersants, antifoaming nonionic agents, and viscosity stabilizers.

U.S. Pat. No. 5,650,543 discloses ethoxylated acetylenic glycols of the form

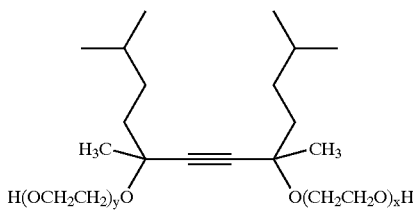

where x and y are integers and the sum is from 2–50. These surfactants are notable because they impart an ability to formulate coating and ink compositions capable of high-speed application.

JP 2636954 B2 discloses propylene oxide adducts of formula

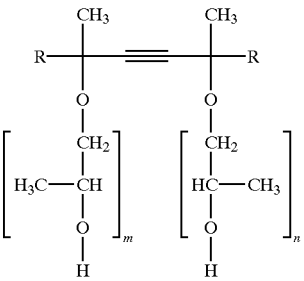

where R=C1–8 alkyl; m+n=integer 1 to 100. These compounds are prepared by reacting acetylenic glycols and propylene oxide in the presence of Lewis acid catalysts such as $BF_3$. It is stated that amine catalysts are inactive for the addition of propylene oxide to acetylenic diols. The propylene oxide adducts are said to be useful as wettability improvers for antitrust oil, antifoamers, spreaders for pesticides, and wetting agents for adhesives. They are effective in improving wettability of oils and have improved antifoaming ability.

JP 2621662 B2 describes dye or developing agent dispersions for thermal recording paper containing propylene oxide (PO) derivatives of an acetylenic diol of the form

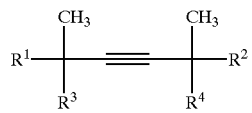

where R1 and R2 are —CH3, —C2H5, —C4H9; R3 and R4 are —(OC3H4)mOH, or —OH where m is an integer 1–10.

JP 04071894 A describes coating solutions containing a dispersion of a colorless electron donating dye precursor and a dispersion of developer. At least one of them contains at least one type of wax having a melting point of at least 60° C. and at least one EO or PO derivative of an acetylenic diol of the formula

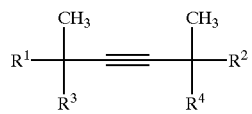

where R1 and R4 each represent methyl, ethyl, propyl, or butyl and R2 and R3 are each —(OC2H5)nOH, or —(OC3H6)nOH (n is 1–10), or OH, mixed and dispersed.

JP 2569377 B2 discloses a recording material containing dispersions of a substantially colorless electron donating dye precursor and a developer. When at least one of these dispersions is prepared, at least one of the compounds

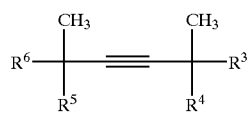

where $R^3$ and $R^6$=methyl, ethyl, propyl or butyl; and $R^4$ and $R^5$=—$(OC_2H_4)_m OH_1$—$(OC_3H_6)_m OH$ (where m=an integer of 1–10) or —OH is added.

JP 09150577 A discloses a heat sensitive recording medium which contains in the heat sensitive layer a leuco dye and 0.1–1.0 wt % of an ethoxylate or propoxylate of an acetylenic glycol of the form

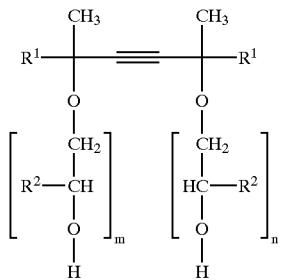

where $R^1$=methyl, ethyl, propyl or butyl; $R^2$=hydrogen or methyl; and n and m=1–10.

JP 04091168 A discloses silica which has been surface treated with compounds of the form

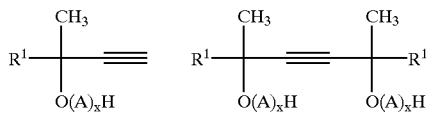

where R1=1–8C alkyl, A=2–3C alkylene glycol residue, R1 and A in a molecule may be the same or different, x and y=each an integer of 0–25.

JP 06279081 A describes a manufacturing process for a cement mortar-concrete hardening material to which 0.5–10 wt. % an acetylenic alcohol or diol alkoxylate is added together with fluorine group surfactants and/or silicon group surfactants. The acetylenic material can be expressed by the formula

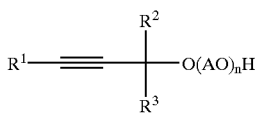

where R1=H or —C(R2)(R3)(O(AO)nH); R2 and R3=1–8C alkyl radicals, A=2–3C alkylene radicals and n=0–30.

JP 03063187 A discloses the use of acetylenic glycol ethylene oxide and/or propylene oxide addition products in concentrated aqueous fountain solution compositions for offset printing. In one example, the 8 to 12 mole ethylene oxide/1 to 2 mole propylene oxide adduct of 3,5-dimethyl-4-octyne-3,5-diol is used in a fountain solution. Other examples illustrate the use of only ethylene oxide derivatives of acetylenic diols.

Although acetylenic diol derivatives containing both ethylene oxide (EO) and propylene oxide (PO) have been taught as a general class of materials, usually as potential extensions of work which had been performed with ethylene oxide derivatives, no actual examples of an acetylenic diol EO/PO derivative based upon 2,4,7,9-tetramethyl-5-decyne-4,7-diol or 2,5,8,11-tetramethyl-6-dodecyne-5,8-diol have been prepared and evaluated. There are no disclosures of any process that could be used to prepare materials of this type.

The use of surfactants in photoresist developer compositions has been known for at least two decades.

U.S. Pat. No. 4,374,920 discloses using a non-ionic surfactant in an aqueous alkaline developer composition for positive-working lithographic printing plates and photoresists. The surfactant was tetramethyl decynediol or ethoxylated tetramethyl decynediol. The specific surfactants were SURFYNOL® 440, 465 and 485 surfactants of Air Products and Chemicals, Inc.

U.S. Pat. No. 4,833,067 discloses aqueous developing solutions for positive-working photoresist compositions containing an organic basic compound free from metallic ions, such as tetramethylammonium hydroxide and choline, as the main ingredient and 50 to 5000 ppm of an acetylenic alcohol. These aqueous developing solutions are said to have increased surface wetting and decreased foaming.

U.S. Pat. No. 5,069,996 discloses photoresist developer compositions containing TMAH, novolak resin, an ethoxylated tetramethyidecynediol surfactant, a defoamer and water.

U.S. Pat. No. 5,756,267 discloses developing solutions useful in the manufacture of liquid crystal displays. These solutions contain water, a quaternary ammonium base such as TMAH, a quaternary ammonium salt surface active agent, an alkanolamine and an acetylenic alcohol based surface active agent which is the same as those disclosed by the '067 patent.

U.S. Pat. No. 5,922,522 discloses developing solutions for photoresists containing an anti-scum agent which is a mixture of an ethoxylate surfactant and a propoxylate surfactant. Although no example of such a compound is given, it is said that the ethylene oxide units and the propylene oxide units can be incorporated in a chain in the same molecule. These surfactants are said to be preferably anionic and have a hydrophobic end on the molecule formed from alcohols such as nonylphenol, octylphenol, and tristyrylphenol.

JP 10-319606 discloses a photoresist developer containing water, alkaline substance, and a block copolymer having the formula HO—A—B—A—H wherein A and B are a polyethylene oxide group or a polypropylene oxide group, the molecule containing both groups. These block copolymers, however, are very susceptible to forming micelles which can cause surface defects in microelectronic applications.

In spite of all the advances in this field of semiconductor manufacture, the need continues to exist for new surfactants which can efficiently lower surface tension in a developer as it is applied to an exposed photoresist while minimizing foam production.

SUMMARY OF THE INVENTION

This invention provides alkoxylated acetylenic diols that act as surfactants for water based compositions of the following structure:

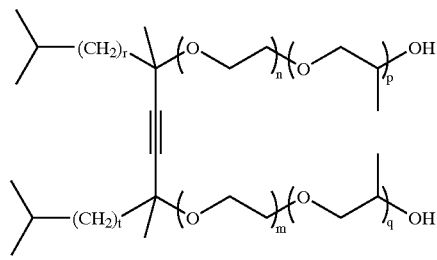

where r and t are, preferably the same, 1 or 2, (n+m) is 1 to 30 and (p+q) is 1 to 30. The EO and PO units may be distributed along the alkylene oxide chain in blocks of EOs and POs or randomly.

This invention also relates to processes for the manufacture of certain alkoxylated acetylenic diols.

Another embodiment of the invention affords water-based compositions containing an organic or inorganic compound, particularly aqueous organic coating, ink, agricultural and electronics cleaning compositions, having reduced equilibrium and dynamic surface tension by incorporation of an effective amount of an alkoxylated acetylenic diol of the above structure.

By "water-based", "aqueous" or "aqueous medium" we mean, for purposes of this invention, a solvent or liquid dispersing medium which comprises at least about 90 wt %, preferably at least about 95 wt %, water. Obviously, an all water medium is also included and is most preferred. Also for purposes of the present invention, the terms "photoresist developing" and "electronics cleaning" are interchangeable.

It is desirable that an aqueous solution of the alkoxylated acetylenic diol demonstrates a dynamic surface tension of less than 35 dynes/cm at a concentration of ≦0.5 wt % in water at 23° C. and 1 bubble/second according to the maximum-bubble pressure method. The maximum-bubble-pressure method of measuring surface tension is described in *Langmuir* 1986, 2, 428–432, which is incorporated by reference.

Also provided is a method for lowering the equilibrium and dynamic surface tension of aqueous compositions by the incorporation of these alkoxylated acetylenic diol compounds.

Also provided is a method for applying a water-based inorganic or organic compound-containing composition to a surface to partially or fully coat the surface with the water-based composition, the composition containing an effective amount of an alkoxylated acetylenic diol compound of the above structure for reducing the dynamic surface tension of the water-based composition.

There are significant advantages associated with the use of these alkoxylated acetylenic diols in water-based organic coatings, inks, fountain solutions for gravure printing processes, agricultural and electronics cleaning compositions and these advantages include:

- an ability to formulate water-borne compositions which may be applied to a variety of substrates with excellent wetting of substrate surfaces including contaminated and low energy surfaces;
- an ability to provide a reduction in coating or printing defects such as orange peel and flow/leveling deficiencies;
- an ability to produce water-borne coatings, fountain solutions and inks which have low volatile organic content, thus making these alkoxylated acetylenic diol surfactants environmentally favorable;
- an ability to formulate coating, fountain solution and ink compositions capable of high speed application;
- an ability to control the foaming characteristics of the water-based compositions;
- an ability to formulate low surface tension aqueous electronics cleaning and processing solutions, including photoresist developer solutions, for the semiconductor manufacturing industry with good wetting and extremely low foam; and
- an ability to produce some members of the class using a chemical process similar to that used to produce acetylenic diol ethoxylates.

Because of their excellent surfactant properties and the ability to control foam, these materials are likely to find use in many applications in which reduction in dynamic and equilibrium surface tension and low foam are important. Such uses include various wet-processing textile operations, such as dyeing of fibers, fiber souring, and kier boiling, where low-foaming properties would be particularly advantageous; they may also have applicability in soaps, water-based perfumes, shampoos, and various detergents where their marked ability to lower surface tension while simultaneously producing substantially no foam would be highly desirable.

The use of these materials in photoresist developer formulations is of particular importance because of their ability to provide all the advantages of surface tension lowering plus outstanding performance in reducing the formation of foam.

DETAILED DESCRIPTION OF THE INVENTION

This invention relates to compounds of the formulas A and B.

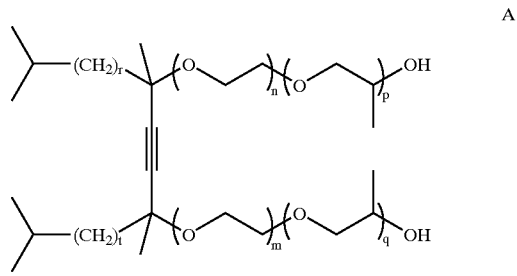

where (n+m) and (p+q) each can range from 1 to 30. It is preferred that (n+m) be 1.3 to 15 and most preferably 1.3 to 10. It is preferred that (p+q) be 1 to 10, more preferred 1–3 and most preferred 2. In Formula A, r and t are 1 or 2, especially r=t, i.e. the acetylenic diol portion of the molecule is 2,4,7,9-tetramethyl-5-decyne-4,7-diol or 2,5,8,11-tetramethyl-6-dodecyne-5,8-diol.

The alkylene oxide moieties represented by (OC2H4) are the (n+m) polymerized ethylene oxide (EO) units and those represented by (OC3H6) are the (p+q) polymerized propylene oxide (PO) units. Products in which the EO and PO units are each segregated together are referred to as "block" alkoxylate derivatives. It is preferred the block copolymer products be capped, i.e., endcapped, with PO units.

The products in which the EO and PO units are randomly distributed along the polymer chain are referred to as "random" alkoxylate derivatives. Random derivatives can be represented by formula B

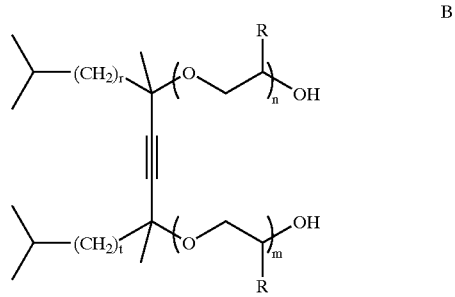

where R is hydrogen or methyl and (n+m)=2–60 with the proviso that the compound contain at least one ethylene oxide, preferably at least 1.3 EO units, and at least one propylene oxide unit, preferably at least 2 PO units, and r and t are 1 or 2, especially r=t.

The block compositions of structure A can be prepared by reaction of 2,4,7,9-tetramethyl-5-decyne-4,7-diol or 2,5,8, 11-tetramethyl-6-dodecyne-5,8-diol with the requisite quantities of ethylene oxide followed by propylene oxide in the presence of a suitable catalyst. Suitable catalysts include trialkylamines and Lewis acids, particularly $BF_3$. Alternatively, the compositions may be prepared by reaction of a pre-formed acetylenic diol ethoxylate with propylene oxide in the presence of an appropriate catalyst. In this case of a pre-formed acetylenic diol ethoxylate, it may be possible to use KOH or other alkali catalysts to effect the reaction with propylene oxide, provided the amount of ethylene oxide which has been added is sufficient to cover essentially all of the tertiary alcohol functionality.

The preferred process for making the acetylenic diol alkoxylates uses $BF_3$ or trialkylamine catalysts. The use of $BF_3$ allows the rapid preparation of derivatives containing relatively large quantities of propylene oxide. However, compositions prepared with trialkylamine catalysts, especially trimethylamine, are preferred for several reasons. They can be prepared using a process very similar to that used for manufacture of acetylenic diol ethoxylates without significant byproduct chemistry. In particular, trialkylamine catalysts allow for the preparation of 2 mole propylene oxide capped derivatives in high selectivity using a highly efficient, one pot process.

With respect to the processes for the preparation of acetylenic diol EO/PO adducts, the tertiary acetylenic diol starting materials can be prepared in various known manners such as those described in U.S. Pat. Nos. 2,250,445; 2,106,180 and 2,163,720, which are incorporated by reference. The acetylenic diol starting material may contain from 8 to 26 carbons. It is preferred that the acetylenic diol starting material contain 14 to 16 carbons, and it is most particularly preferred that it be 2,4,7,9-tetramethyl-5-decyne-4,7-diol or 2,5,8,11-tetramethyl-6-dodecyne-5,8-diol.

Various basic catalysts can be used to promote the reaction between the alkylene oxide and the acetylenic tertiary glycols in which the hydroxyl groups are attached to a carbon atom in a position alpha to the acetylenic bonds according to this invention. Tertiary aliphatic amines, namely trialkylamines such as trimethylamine, triethylamine, tripropylamine, dimethylethylamine, diethylmethylamine and the like, are particularly advantageous catalysts for the reaction. Such tertiary aliphatic amines catalyze the addition reaction at a rapid rate at moderately low temperatures and pressures without inducing cleavage of the acetylenic glycol. Trimethylamine is preferred because of its high catalytic activity and longevity in the reaction.

As is known in the art, the use of strongly basic catalysts such as sodium hydroxide, especially at high temperatures of about 150° C., induces cleavage of the acetylenic tertiary glycols and for this reason should be avoided, unless of course, sufficient ethylene oxide has been added to prevent substantial decomposition of tertiary acetylenic alcohol functionality. Once the tertiary hydroxyl groups of the acetylenic glycol have reacted with ethylene oxide, the resultant adduct exhibits the marked stability of an ether. So stable are the adducts that they can be heated with concentrated base such as sodium hydroxide at elevated temperatures, while comparable treatment of the initial acetylenic glycol is accompanied by extensive degradation. Consequently, strongly basic catalysts, such as the alkali metal hydroxides, can be used to increase the polyalkylene oxide chain length once the initial adducts have been formed and protected against decomposition. It is anticipated that alkali metal hydroxides could also be used to promote the addition of propylene oxide to initial EO or PO adducts with sufficiently low quantities of residual tertiary acetylenic alcohol functionality.

The trialkylamine-catalyzed addition reaction may be performed at either atmospheric (15 psig; 1 bar) or moderate to low superatmospheric pressures (30–300 psig; 2–20 bar). The use of moderate to low superatmospheric pressures is preferred since it obviates the necessity of recycling unreacted ethylene oxide and propylene oxide, and generally proceeds at faster rates than additions carried out at atmospheric pressures. The effect of pressure on rate is particularly important in the reaction with propylene oxide, and it is therefore preferred that reactions be performed at pressures in excess of 30 psig (2 bar). It is particularly preferred that the process be carried out at a pressure greater than 60 psig (4 bar). Another benefit of performing the reaction under pressure is that such reactions may be accomplished with ordinary efficient agitation, while reactions conducted at atmospheric pressure often work best when a dispersion type agitator is used. While the reaction can be carried out at lower pressure, reaction rates, and therefore reactor productivity, suffer. Performing the reaction at pressures much in excess of about 300 psig (20 bar) would likely have only marginal benefit, and would increase the cost of equipment required for manufacture. It is preferred to operate at 100 psig (6.7 bar).

The temperature at which the reaction is run for trialkylamine catalyzed reactions will depend upon the particular system and the catalyst concentration. Generally, at higher catalyst concentrations, the reactions can be run at lower temperatures and pressures. Reaction temperatures should be high enough to permit the reaction to proceed at a reasonable rate, but low enough to prevent decomposition of the reagents and products. Temperatures in the range of 40–150° C. are suitable, 50–120° C. preferred, and 70–90° C. particularly preferred.

In the trialkylamine catalyzed process in which propylene oxide is added to an acetylenic diol EO adduct, the reaction stops at a PO end cap on each chain, i.e., the obtained product is an acetylenic diol EO/PO adduct containing two PO end caps, p and q each being 1 in Formula A. When a mixture of EO and PO is added to an acetylenic diol or diol EO adduct, the trialkylamine catalyzed process affords an adduct having random EO and PO units, in the latter case extending beyond the original EO block.

To prepare the EO/PO adducts of the invention, the acetylenic glycol is liquefied by melting and the catalyst is added with stirring. Ethylene oxide and/or propylene oxide are added as liquids with stirring and the reaction is concluded when the desired polyalkylene oxide chain length is reached as determined by gel permeation chromatography (GPC), high performance liquid chromatography (HPLC), nuclear magnetic resonance (NMR), cloud point (ASTM D2024-65) or water titration of an isopropyl alcohol solution. No solvents are necessary during the reaction, but inert solvents such as aromatic hydrocarbons (benzene and toluene) and ethers (ethyl ether) may be used to facilitate handling. In some instances it may be convenient to use a low mole ethoxylated acetylenic diol, since these products are liquids and are therefore easy to handle.

In reactions catalyzed by Lewis acids, the reaction conditions will be determined by the identity and concentration of the catalyst. Examples of Lewis acid catalysts include $BCl_3$, $AlCl_3$, $TiCl_4$, $BF_3$, $SnCl_4$, $ZnCl_2$ and the like. The preferred Lewis acid catalyst is $BF_3$. In $BF_3$ catalyzed reactions, temperature control during the initial stages of the reaction is critical, since too high a temperature will result in dehydration of the acetylenic diol. It is preferred that the temperature be maintained below 80° C., preferably below 60° C., and most preferably below 50° C. The reaction pressure can range from atmospheric to low to moderate superatmospheric pressure, i.e., from 15 to 300 psig (1 to 20 bar). Because of the high activity of $BF_3$, good results can be obtained at more moderate pressures of about 1 bar than for those reactions performed using trialkylamine catalysts.

In adding liquid alkylene oxide(s) to the acetylenic glycol and the catalyst, care should be taken to avoid the presence of an excess of alkylene oxide(s) in the reaction mixture since the reaction is very exothermic and could prove to be very hazardous. The danger of an uncontrollable reaction can be avoided by adding the alkylene oxide(s) in a manner and at a rate such that the alkylene oxide(s) are reacted essentially as rapidly as they are introduced into the reaction mixture. The formation of a flammable mixture in the headspace is best avoided by pressuring the reactor headspace to a sufficient pressure with an inert gas such as nitrogen such that the alkylene oxide(s) remains below its lower explosive limit (LEL).

In the both the Lewis acid catalyzed and the trialkylamine catalyzed processes, the catalysts may be used at 0.001 to 10 wt %, preferably 0.01 to 5 wt %, and most preferably 0.1 to 1 wt %, based on total final reactant mass. In both cases, because deactivation may occur during the alkoxylation, it may be necessary to add additional catalyst to complete the reaction, particularly if large amounts of EO and PO are being added.

In the processes for making the randomly distributed EO/PO adducts, the EO and PO may be added to the reaction concurrently as separate charges or streams, or added as a single charge or stream comprising a mixture of EO and PO. In making block EO/PO adducts the EO and PO are added consecutively.

The alkoxylated acetylenic diols are useful for the reduction of equilibrium and dynamic surface tension in water-based compositions containing an organic compound, particularly aqueous coating, ink, fountain solution, agricultural and electronics processing compositions containing organic compounds such as polymeric resins, macromolecules, organic bases, herbicides, fungicides, insecticides or plant growth modifying agents. It is desirable that an aqueous solution of the alkoxylated acetylenic diol demonstrates a dynamic surface tension of less than 35 dynes/cm at a concentration of $\leq 0.5$ wt % in water at 23° C. and 1 bubble/second according to the maximum-bubble-pressure method. The maximum-bubble-pressure method of measuring surface tension is described in *Langmuir* 1986, 2, 428–432, which is incorporated by reference.

In one aspect of the invention certain alkoxylated acetylenic diols of the above formula display excellent ability to reduce equilibrium and dynamic surface tension while producing substantially no foam. This behavior is particularly advantageous in photoresist developer formulations.

The alkoxylated acetylenic diols are suitable for use in an aqueous composition comprising in water an inorganic compound which is, for example, a mineral ore or a pigment or an organic compound which is a pigment, a polymerizable monomer, such as addition, condensation and vinyl monomers, an oligomeric resin, a polymeric resin, a macromolecule such as gum arabic or carboxymethyl cellulose, a detergent, a caustic cleaning agent, a dissolution agent such as tetramethylammonium hydroxide (TMAH), a herbicide, a fungicide, an insecticide, or a plant growth modifying agent.

An amount of the alkoxylated acetylenic diol compound that is effective to reduce the equilibrium and/or dynamic surface tension of the water-based, organic or inorganic compound-containing composition is added. Such effective amount may range from 0.001 to 10 g/100 mL, preferably 0.01 to 1 g/100 mL, and most preferably 0.05 to 0.5 g/100 mL of the aqueous composition. For water-based photoresist developer/electronics cleaning compositions effective amounts may range from 0.001 to 1 g/100 mL, preferably 0.002 to 0.8 g/100 mL, and most preferably 0.005 to 0.5 g/100 mL. Naturally, the most effective amount will depend on the particular application and the solubility of the particular alkoxylated acetylenic diol.

In the following water-based organic coating, ink, fountain solution and agricultural compositions containing an alkoxylated acetylenic diol according to the invention, the other listed components of such compositions are those materials well known to the workers in the relevant art.

A typical water-based protective or decorative organic coating composition to which the alkoxylated acetylenic diol surfactants of the invention may be added would comprise the following components in an aqueous medium at 30 to 80 wt % ingredients:

| Water-Based Organic Coating Composition | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting Agent/Flow and Leveling Agents |
| 0.01 to 5 wt % | Acetylenic Diol EO/PO Derivative |

A typical water-based ink composition to which the alkoxylated acetylenic diol surfactants of the invention may be added would comprise the following components in an aqueous medium at 20 to 60 wt % ingredients:

| Water-Based Ink Composition | |
|---|---|
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing Solvents |
| 0.01 to 10 wt % | Surfactant/Wetting Agent |
| 0.01 to 10 wt % | Processing Aids/Defoamers/Solubilizing Agents |
| 0.01 to 5 wt % | Acetylenic Diol EO/PO Derivative |

A typical water-based agricultural composition to which the alkoxylated acetylenic diol surfactants of the invention may be added would comprise the following components in an aqueous medium at 0.1 to 80 wt % ingredients:

| Water-Based Agricultural Composition | |
|---|---|
| 0.1 to 50 wt % | Insecticide, Herbicide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.01 to 50 wt % | Acetylenic Diol EO/PO Derivative |

A typical fountain solution composition for planographic printing to which the alkoxylated acetylenic diol surfactants of the invention may be added would comprise the following components in an aqueous medium at 30 to 70 wt % ingredients:

| Fountain Solution for Planographic Printing | |
|---|---|
| 0.05 to 30 wt % | Film formable, water soluble macromolecule |
| 1 to 75 wt % | Alcohol, glycol, or polyol with 2–12 carbon atoms, water soluble or can be made to be water soluble |
| 0.01 to 60 wt % | Water soluble organic acid, inorganic acid, or a salt of thereof |
| 0.01 to 50 wt % | Acetylenic Diol EO/PO Derivative |

Other compositions in which use of the acetylenic diol EO/PO adduct as a surfactant is particularly advantageous are the developers for photoresists that are employed in the semiconductor industry. Such developers and their use are well known in the art and do not need to be described in detail. In fact, as pointed out in the background section of this disclosure, the use of ethoxylated acetylenic diol adducts in such formulations is known and well documented. The improvement provided by this invention, which could not have been foreseen, involves the use in these developer formulations of certain acetylenic diol adducts which also contain propoxy groups.

A typical water-based photoresist developer, or electronic cleaning, composition to which the alkoxylated acetylenic diol surfactants of the invention may be added would comprise an aqueous medium containing the following components:

| Water-Based Photoresist Developer Composition | |
|---|---|
| 0.1 to 3 wt % | Tetramethylammonium Hydroxide |
| 0 to 4 wt % | Phenolic Compound |
| 10 to 10,000 ppm | Acetylenic Diol EO/PO Deriviative |

Briefly, the process for manufacture of integrated circuits involves the application of a film of photoresist composition to a suitable substrate, such as a silicon wafer, which is then exposed to actinic radiation in a designed pattern that is imposed upon the photoresist film. Depending upon whether the photoresist is positive or negative-working, the radiation either increases or decreases its solubility in a subsequently applied developer solution. Consequently, in a positive-working photoresist the areas masked from the radiation remain after development while the exposed areas are dissolved away. In the negative-working photoresist the opposite occurs. The surfactant of this invention can be used in developers for either type of photoresist. The character of the developer is very important in determining the quality of the circuits formed and precise control of developing is essential. To achieve better surface wetting by the developer is has been common to add surfactant to the formulation in order to reduce surface tension of the solution. This addition, however, can cause the developer to foam which leads to circuit defects. This foaming problem is also recognized in the art and considerable attention in the industry has been directed toward its solution.

The developer, or electronics cleaning, solutions in which use of the adduct of the invention is preferred are the aqueous solutions of tetramethylammonium hydroxide (TMAH). These developers are also well known in the art. Commercial developers usually contain low levels of surfactant on the order of 50 to 1000 ppm by weight. Surfactant level should not exceed that required to achieve the desired surface tension of the solution. For example, surface tensions of about 40 to 45 dynes/cm would be appropriate for novolac-based photoresist resins. Advanced resins that often incorporate aliphatic groups might require a developer with lower surface tension to enhance wetting. One of the advantages of the surfactants of this invention is that suitable surface tensions can be obtained at lower levels than is required by other wetting agents. This in itself is a step toward solving the foaming problem in the manufacture of microcircuitry.

EXAMPLE 1

This example illustrates that two mole propoxylates of acetylenic diol ethoxylates can be prepared with high selectivity when using trialkylamine catalysts. In this example, the preparation of the 7 mole propoxylate of Surfynol® 465 surfactant, which is the 10 mole ethoxylate of 2,4,7,9-tetramethyl-4-decyne-4,7-diol, was attempted.

A 1000 mL autoclave was charged with Surfynol® 465 surfactant (300 g, 0.45 moles) and dimethylethylamine (53.7 g, 0.73 moles). The reactor was sealed, purged free of air with three nitrogen pressure-vent cycles, then pressured to 100 psig (6.7 bar) with nitrogen and heated to 120° C. Propylene oxide (183 g, 3.15 moles) was added over a period of 70 minutes by means of a syringe pump. At the completion of the addition, the reaction mixture was heated for an additional 12 hr at 120° C. The reactor contents were cooled and discharged. The product was heated under vacuum to remove volatiles (unreacted PO and catalyst); 68 g of material were removed.

Matrix assisted laser desorption/ionization mass spectrometry (MALD/I) indicated that almost all the individual oligomers in the product possessed one or two propylene oxide residues with only very small amounts of product containing three or more PO units. The fate of a substantial amount of the propylene oxide appeared to be formation of dimethylamino-terminated polypropyleneoxide.

These results are consistent with relatively facile reaction of primary hydroxyl with propylene oxide, but only very sluggish reaction of propylene oxide terminated chains. It appears that after EO-terminated chains react with one propylene oxide, chain growth essentially stops. Since there are approximately two EO chains for each starting acetylenic diol, high selectivity to the two-mole propoxylate results. In this environment, decomposition of the catalyst to form dimethylamino-terminated polypropylene oxide is the predominant reaction.

It would not be anticipated based on the teachings of JP 2636954 B2 that trialkylamine catalysts would have any efficacy for promoting the reaction of propylene oxide. It would also not be anticipated that high selectivity to the two mole propoxylates of an acetylenic diol could be achieved.

EXAMPLES 2–5

Example 3 illustrates the preparation of the 3.5 mole ethoxylate of 2,4,7,9-tetramethyl-5-decyne-4,7-diol capped with 2 moles of propylene oxide using trimethylamine catalyst and a preformed ethoxylate. The 3.5 mole ethoxylate of 2,4,7,9-tetramethyl-5-decyne-4,7-diol is commercially available from Air Products and Chemicals, Inc. and is marketed as Surfynol® 440 surfactant.

A 1000 mL autoclave was charged with Surfynol® 440 surfactant (400 g, 1.05 moles) which had previously been dried by heating under nitrogen. The reactor was sealed and pressure checked, the air was removed with three nitrogen pressure-vent cycles, and trimethylamine (2.7 g, 0.5 wt % of final reaction mass) was added by means of a gas tight syringe. The reactor was pressured to 100 psig (6.7 bar) with nitrogen and heated to 100° C. whereupon propylene oxide (122 g, 147 mL, 2.10 moles) was added at a rate of 1.0 mL/min by means of a syringe pump. At the completion of the addition, the reactor contents were stirred at 100° C. for 14.5 hours. The reactor was cooled and the contents were discharged into a round bottomed flask and heated under vacuum (0.25 torr) at ambient temperature (ca. 23° C.) for 16 hours to remove the trimethylamine catalyst. The product was characterized by nuclear magnetic resonance (NMR) spectrometry. The data are summarized in Table 1 which shows acetylenic diol compositions prepared using trimethylamine catalysis.

Other ethylene oxide/propylene oxide derivatives of 2,4,7,9-tetramethyl-5-decyne-4,7-diol (Examples 2, 4 and 5) were prepared in a similar manner. The compositions are also summarized in Table 1.

Since JP 2636954 B2 states that amines are inactive for the addition of propylene oxide, it would not be anticipated that trimethylamine would be an effective catalyst for the preparation of an EO/PO derivative of 2,4,7,9-tetramethyl-5-decyne-4,7-diol.

TABLE 1

| | Theoretical | | Determined by NMR | |
|---|---|---|---|---|
| Example | EO Moles | PO Moles | EO Moles | PO Moles |
| 2 | 1.3 | 2.0 | 1.5 | 1.9 |
| 3 | 3.5 | 2.0 | 39 | 2.08 |
| 4 | 5.1 | 2.0 | 5.9 | 2.0 |
| 5 | 10.0 | 2.0 | 10.7 | 2.0 |

EXAMPLES 6–21

These examples illustrate the preparation of ethylene oxide/propylene oxide derivatives of 2,4,7,9-tetramethyl-5-decyne-4,7-diol (designated S104) and 2,5,8,11-tetramethyl-6-dodecyne-5,8-diol (designated S124) using $BF_3$ catalyst. To our knowledge a procedure for the preparation of ethylene oxide/propylene oxide derivatives of acetylenic diols using Lewis acids such as $BF_3$ has not previously been disclosed. The procedure is illustrated for the preparation of the 5 mole ethylene oxide, 2 mole propylene oxide adduct of 2,4,7,9-tetramethyl-5-decyne-4,7-diol (Sl04) in which the EO and PO units are randomly situated along the alkylene oxide chain.

A 1000 mL autoclave was charged with the 1.3 mole ethylene oxide adduct of 2,4,7,9-tetramethyl-5-decyne-4,7-diol (313 g, 1.1 moles; Surfynol 104 surfactant from Air Products and Chemicals, Inc.) which had previously been dried by heating under vacuum. The reactor was sealed and pressure checked, the air was removed with three nitrogen pressure-vent cycles. The reactor was pressured to 100 psig (6.7 bar) with nitrogen, and the contents were heated to 40° C. $BF_3$ diethyl etherate (1.3 g) was added and ethylene oxide and propylene oxide were added simultaneously at rates of 91.05 mL/h and 68.95 mL/h, respectively, by means of two syringe pumps. The total amount of ethylene oxide (180 g, 204 mL, 4.08 moles) and propylene oxide (128 g, 155 mL, 2.2 moles) were such that the final mole ratio of diol:EO:PO was 1:5:2. After the completion of the addition, an additional 0.7 g of $BF_3$ diethyl etherate was added, whereupon an exotherm to 45.5° C. was observed. At this point gas chromatographic analysis indicated that the reaction was complete. The product (Example 6) was analyzed by NMR and MALD/I and found to have a structure consistent with the desired structure.

Sixteen similar materials (Examples 7–22) were prepared by variation of the diol structure, the amounts of ethylene oxide and propylene oxide, and the structural motif of the alkylene oxide chain. Table 2 shows the acetylenic diol compositions prepared using $BF_3$ catalysis. In Table 2, R designates "random," while B designates "block."

The composition of Example 22 has been disclosed in JP 03063187 A (however, JP '187 does not teach a method for its preparation nor whether the adduct is a block or random copolymer), and has been shown to have efficacy in fountain solutions for lithographic printing. The S82 designation corresponds to 3,6-dimethyl-4-hexyne-3,6-diol.

TABLE 2

| | | | Theoretical | | Determined by NMR | |
|---|---|---|---|---|---|---|
| Example | Diol | R/B | EO Moles | PO Moles | EO Moles | PO Moles |
| 6 | S104 | R | 5 | 2 | 6.5 | 2.9 |
| 7 | S104 | B | 5 | 2 | 5.5 | 2.2 |
| 8 | S104 | R | 5 | 10 | 3.2 | 11.5 |
| 9 | S104 | B | 5 | 10 | 3.5 | 11.1 |
| 10 | S104 | R | 15 | 2 | 16.2 | 2.2 |
| 11 | S104 | B | 15 | 2 | 14.4 | 2.1 |
| 12 | S104 | R | 15 | 10 | 17.3 | 8.6 |
| 13 | S104 | B | 15 | 10 | 15.0 | 9.7 |
| 14 | S124 | R | 5 | 2 | 6.9 | 3.2 |
| 15 | S124 | B | 5 | 2 | 4.8 | 2.2 |
| 16 | S124 | R | 5 | 10 | 8.0 | 7.6 |
| 17 | S124 | B | 5 | 10 | 5.1 | 10.0 |
| 18 | S124 | R | 15 | 2 | 16.3 | 1.9 |
| 19 | S124 | B | 15 | 2 | 14.9 | 2.1 |
| 20 | S124 | R | 15 | 10 | 15.4 | 9.3 |
| 21 | S124 | B | 15 | 10 | 13.6 | 5.1 |
| 22 | S82 | B | 10 | 2 | 9.6 | 1.9 |

In the following Examples dynamic surface tension data were obtained for aqueous solutions of various compounds using the maximum bubble pressure method at bubble rates from 0.1 bubbles/second (b/s) to 20 b/s. The maximum bubble pressure method of measuring surface tension is described in Langmuir 1986, 2, 428–432. These data provide information about the performance of a surfactant at conditions from near-equilibrium (0.1 b/s) through extremely high surface creation rates (20 b/s). In practical terms, high bubble rates correspond to high printing speeds in lithographic printing, high spray or roller velocities in coating applications, and rapid application rates for agricultural products.

COMPARATIVE EXAMPLE 25

Dynamic surface tension data were obtained for aqueous solutions of the composition of Example 22 (S82/10 EO/2PO/B) using the maximum bubble pressure technique. This material has been disclosed in JP 03063187 A and is taught as a component in an aqueous fountain solution composition. The surface tensions were determined at bubble rates from 0.1 bubbles/second (b/s) to 20 b/s. The data are presented in Table 3.

TABLE 3

Dynamic Surface Tension (dyne/cm)-Example 22

| Concentration (wt %) | 0.1 b/s | 1 b/s | 6 b/s | 15 b/s | 20 b/s |
|---|---|---|---|---|---|
| 0.1 | 39.1 | 42.3 | 46.5 | 51.6 | 53.0 |
| 1.0 | 34.4 | 34.9 | 35.5 | 37.7 | 38.5 |
| 5.0 | 33.8 | 34.0 | 34.7 | 36.3 | 36.4 |

The data illustrate that this product is reasonably effective at reducing the surface tension of water, although relatively high concentrations are required to obtain reasonable performance.

EXAMPLE 26

Solutions in distilled water of 10 mole EO/2 mole PO block derivative of 2,4,7,9-tetramethyl-5-decyne-4,7-diol (Example 5) were prepared and their dynamic surface tension properties were measured using the procedure described above. The data are set forth in the Table 4.

TABLE 4

Dynamic Surface Tension (dyne/cm)-Example 5

| Concentration (wt %) | 0.1 b/s | 1 b/s | 6 b/s | 15 b/s | 20 b/s |
|---|---|---|---|---|---|
| 0.1 | 40.5 | 42.0 | 44.3 | 47.1 | 48.1 |
| 0.5 | 32.4 | 33.6 | 35.1 | 36.6 | 37.2 |
| 1.0 | 29.8 | 30.5 | 32.1 | 33.0 | 33.7 |

These data illustrate that the composition of this invention is markedly superior in its ability to reduce surface tension relative to the composition of the prior art. Comparison of the data for the 1.0 wt % solution of the Example 5 surfactant with that of the 5.0 wt % solution of the S82 derivative (Example 22) shows that the compound of the invention provides superior performance at all surface creation rates at 20% the use level. Since reduction of dynamic surface tension is of such importance in a dynamic application in which aqueous fountain solutions are utilized, it would not be anticipated based on the teachings of the prior art that modification of the hydrophobic group (the acetylenic diol moiety) would have such an advantageous effect.

COMPARATIVE EXAMPLES 27–31

Solutions in distilled water of the 1.3, 3.5, 5.1, and 10 mole ethoxylates of 2,4,7,9-tetramethyl-5-decyne-4,7-diol were prepared. The 1.3, 3.5, and 10 mole ethoxylates are marketed by Air Products and Chemicals, Inc. as Surfynol® 420, 440, and 465 surfactants, respectively. Their dynamic surface tensions were measured using the procedure described above, and these data were used to determine the quantities provided in Table 5.

The $pC_{20}$ value is defined as the negative logarithm of the molar concentration of surfactant required to decrease the surface tension of an aqueous solution to 52.1 dyne/cm, that is, 20 dyne/cm below that of pure water when the measurement is performed at 0.1 b/s. This value is a measure of the efficiency of a surfactant. In general, an increase in $pC_{20}$ value of 1.0 indicates that 10 times less surfactant will be required to observe a given effect.

The critical aggregation concentrations (solubility limit or critical micelle concentration) were determined by intersection of the linear portion of a surface tension/ln concentration curve with the limiting surface tension as is described in many textbooks. The limiting surface tensions at 0.1 and 20 bubbles/second (b/s) represent the lowest surface tensions in water which can be achieved at the given surface creation rate for a given surfactant regardless of the amount of surfactant used. These values give information about the relative ability to a surfactant to reduce surface defects under near-equilibrium condition (0.1 b/s) through very dynamic conditions (20 b/s). Lower surface tensions would allow the elimination of defects upon application of a formulation onto lower energy surfaces.

The foaming properties of 0.1 wt % solutions of the prior art surfactants were examined using a procedure based upon ASTM D 1173-53. In this test, a 0.1 wt % solution of the surfactant is added from an elevated foam pipette to a foam receiver containing the same solution. The foam height is measured at the completion of the addition ("Initial Foam Height") and the time required for the foam to dissipate is recorded ("Time to 0 Foam"). This test provides a comparison between the foaming characteristics of various surfactant solutions. In general, in photoresist developers, coatings, inks, and agricultural formulations, foam is undesirable because is complicates handling and can lead to coating and print defects, and to inefficient application of agricultural materials.

TABLE 5

| Structure | Sol $pC_{20}$ | Limit | limiting γ 0.1 b/s | 20 b/s | γ (0.1% solution) 1 b/s | 6 b/s | RM Foam initial (t to 0) |
|---|---|---|---|---|---|---|---|
| Example 27 Surfynol 104 | 3.74 | 0.1 | 32.1 | 40.3 | 33.1 | 36.4 | 2.0 (3 s) |

TABLE 5-continued

| Structure | pC$_{20}$ | Sol Limit | limiting γ 0.1 b/s | limiting γ 20 b/s | γ (0.1% solution) 1 b/s | γ (0.1% solution) 6 b/s | RM Foam initial (t to 0) |
|---|---|---|---|---|---|---|---|
| Example 28 <br> Surfynol 420 (OH·1.3 EO) | 3.84 | 0.18 | 28.8 | 31.7 | 32.8 | 34.2 | 0.5 (3 s) |
| Example 29 <br> Surfynol 440 (OH·3.5 EO) | 3.90 | 0.29 | 26.9 | 29.3 | 34.3 | 36.2 | 1.4 (9 s) |
| Example 30 <br> Surfynol 450 (OH·5.1 EO) | 3.95 | 0.40 | 26.9 | 29.8 | 36.1 | 38.3 | 1.3 (32 s) |
| Example 31 <br> Surfynol 465 (OH·10 EO) | 3.79 | (0.89) | 29.0 | 32.7 | 42.5 | 44.8 | 1.5 (0.6 cm) |
| Example 32 <br> Surfynol 485 (OH·30 EO) | 3.43 | (2.91) | 35.7 | 39.9 | 51.5 | 53.2 | 1.5 (0.6 cm) |

EXAMPLES 33–36

Surface tension and foam data were obtained in a similar manner for the surfactants of Examples 1–4 based on 2,4,7,9-tetramethyl-5-decyne-4,7-diol. The data are set forth in Table 6.

TABLE 6

| Structure | pC$_{20}$ | Sol Limit | limiting γ 0.1 b/s | limiting γ 20 b/s | γ (0.1% solution) 1 b/s | γ (0.1% solution) 6 b/s | RM Foam Initial (t to 0) |
|---|---|---|---|---|---|---|---|
| Example 33 <br> 1.3 EO/2 PO <br> (Example 2) | 3.51 | 0.07 | 31.6 | 40.6 | 33.4 | 40.6 | 1.6 (3s) |
| Example 34 <br> 3.5 EO/2 PO <br> (Example 3) | 4.07 | 0.21 | 29.3 | 31.4 | 33.6 | 36.6 | 1.0 (10 s) |
| Example 35 <br> 5.1 EO/2 PO <br> (Example 4) | 4.13 | 0.32 | 27.3 | 29.9 | 35.3. | 37.6 | 0.3 (6 s) |

TABLE 6-continued

| Structure | pC$_{20}$ | Sol Limit | limiting γ 0.1 b/s | limiting γ 20 b/s | γ (0.1% solution) 1 b/s | γ (0.1% solution) 6 b/s | RM Foam Initial (t to 0) |
|---|---|---|---|---|---|---|---|
| Example 36 10 EO/2 PO (Example 5) | 4.05 | (0.78) | 29.8 | 33.7 | 42.0 | 44.3 | 2.1 (1.3) |

The data in Table 6 illustrate that propoxylation with 2 moles of propylene oxide in the presence of trimethylamine resulted in surfactants with higher efficiencies than their unpropoxylated counterparts. This effect is reflected in both the pC$_{20}$ values, which increase by about 0.2 units, and the surface tension results for 0.1 wt % solutions at 1 b/s, which decrease by about a dyne/cm. In addition, the foaming characteristics of the surfactants change significantly as a result of modification with propylene oxide. This change can be either in the direction of greater foam (e.g. for the 10 and 30 mole ethoxylates) or to lesser foam (for the 5.1 mole ethoxylate). The ability to control foam is advantageous in many applications, including photoresist developers, coatings, inks, adhesives, fountain solutions, agricultural formulations, soaps and detergents.

EXAMPLES 37–52

Solutions in distilled water of the materials of Examples 37–52 were prepared and their surface tension and foam performance were evaluated as in the example above. The results are set forth in the Table 7.

TABLE 7

| Structure | pC$_{20}$ | CAG[c] | limiting γ[a] 0.1 b/s | limiting γ[a] 20 b/s | γ (0.1% solution)[a] 1 b/s | γ (0.1% solution)[a] 6 b/s | RM Foam[b] initial (t to 0) |
|---|---|---|---|---|---|---|---|
| Example 37 104/5/2/R (Example 6) | 4.16 | 0.10 | 28.6 | 31.2 | 30.0 | 37.1 | 1.1 (5 s) |
| Example 38 104/5/2/B (Example 7) | 4.15 | 0.11 | 27.9 | 33.1 | 33.6 | 38.4 | 1.9 (4 s) |
| Example 39 104/5/10/R (Example 8) | 4.50 | 0.04 | 31.2 | 35.0 | 33.7 | 39.9 | 0.5 (1 s) |
| Example 40 104/5/10/B (Example 9) | 4.58 | 0.08 | 31.0 | 34.1 | 37.2 | 40.5 | 0.5 (10 s) |
| Example 41 104/15/2/R (Example 10) | 4.20 | 0.07 | 28.3 | 30.7 | 36.0 | 43.8 | 4.5 (1.1 cm) |
| Example 42 104/15/2/B (Example 11) | 5.04 | 0.18 | 27.6 | 31.7 | 36.8 | 42.9 | 5.3 (0.5 cm) |
| Example 43 104/15/10/R (Example 12) | 4.42 | 0.05 | 28.8 | 30.9 | 33.8 | 44.5 | 2.8 (0.7 cm) |
| Example 44 104/15/10/B (Example 13) | 4.35 | 0.09 | 28.3 | 34.4 | 35.5 | 45.6 | 4.0 (0.4 cm) |
| Example 45 124/5/2/R (Example 14) | 4.39 | 0.03 | 26.5 | 30.8 | 28.2 | 33.5 | 2.4 (0.2 cm) |
| Example 46 124/5/2/B (Example 15) | 4.42 | 0.04 | 26.9 | 29.7 | 28.5 | 32.5 | 3.0 (0.3 cm) |
| Example 47 124/5/10/R (Example 16) | 4.57 | 0.02 | 30.3 | 36.7 | 31.8 | 40.8 | 1.8 (0.3 cm) |
| Example 48 124/5/10/B (Example 17) | 4.56 | 0.02 | 31.3 | 36.2 | 33.4 | 40.3 | 1.4 (12 s) |
| Example 49 124/15/2/R (Example 18) | 4.36 | 0.06 | 27.9 | 32.2 | 30.5 | 40.8 | 2.6 (1.3 cm) |
| Example 50 124/15/2/B (Example 19) | 4.16 | 0.02 | 27.9 | 35.6 | 31.1 | 42.5 | 2.5 (1.2 cm) |
| Example 51 124/15/10/R (Example 20) | 4.58 | 0.06 | 29.1 | 32.3 | 32.8 | 43.2 | 2.0 (1.0 cm) |
| Example 52 124/15/10/B (Example 21) | 4.55 | 0.05 | 28.0 | 33.3 | 33.7 | 41.4 | 4.8 (1.0 cm) |

[a] dyne/cm.
[b] Ross-Miles foam: cm (time to 0 foam in seconds or cm after 5 minutes)
[c] Critical aggregation concentration (wt %).

These data illustrate variation of the acetylenic diol structure, the EO and PO content, and the structural motif of these surfactants allows tailoring of the surfactant properties to a specific application. Surfactants with very low foam (Examples 39 and 40) or relatively high foam (Examples 41 and 42) can be produced. In addition, most of these materials exhibit excellent dynamic surface tension performance, as shown by their limiting surface tension values at 20 b/s. The combination of properties will be of value in many applications, including coatings, inks, adhesives, fountain solutions, agricultural formulations, soaps and detergents.

EXAMPLE 53

2,4,7,9-Tetramethyl-5-decyne-4,7-diol was ethoxylated to produce the 5.1 mole ethoxylate using trimethylamine catalyst and a procedure similar to that of Examples 2–5. A small sample was withdrawn, and sufficient propylene oxide was added to produce the 0.4 mole propoxylate. Again a sample was withdrawn. Similarly, more propylene oxide was added to produce the 0.9 and 1.4 mole propylene oxide adducts. In a separate run, the 2.0 mole propoxylate of the 5.1 mole ethoxylate was prepared.

Surface tension (γ) and foam data were obtained for the propoxylates of 5.1 mole ethoxylate of 2,4,7,9-tetramethyl-5-decyne-4,7-diol as described above. The data are set forth in the Table 8.

TABLE 8

| | | | γ (0.1 wt % solution)[a] | | | | | |
|---|---|---|---|---|---|---|---|---|
| Ex | moles PO | $pC_{20}$ | 0.1 b/s | 1 b/s | 6 b/s | 15 b/s | 20 b/s | RM Foam[b] Initial (t to 0) |
| 53A | 0 | 3.95 | 35.1 | 36.2 | 38.1 | 42.0 | 44.4 | 1.6 (0.7 cm) |
| 53B | 0.4 | 3.74 | 34.8 | 35.8 | 37.9 | 42.0 | 44.4 | 1.4 (0.3 cm) |
| 53C | 0.9 | 3.72 | 34.9 | 35.9 | 38.2 | 42.7 | 45.3 | 1.4 (27 s) |
| 53D | 1.4 | 3.79 | 34.6 | 35.9 | 38.3 | 42.0 | 44.5 | 1.2 (21 s) |
| 53E | 2.0 | 4.13 | 34.0 | 35.3 | 37.6 | 41.5 | 43.3 | 0.6 (6 s) |

[a]dyne/cm
[b]Initial foam heights in cm (foam height after 5 min, or time to 0 foam).

The data in Table 8 show that while propoxylation up to 2 PO units had little impact on the surface tension performance of the 5.1 mole ethoxylate of 2,4,7,9-tetramethyl-5-decyne-4,7-diol, it had a significant positive impact on foam control, with greater control observed with higher degrees of propoxylation. Such an effect has not previously been observed with alkoxylated derivatives of acetylenic diols. The ability to control foam is of crucial importance in the application of many waterborne formulations, because foam generally leads to defects.

EXAMPLE 54

In these examples additional ethoxylated acetylenic diols were synthesized.

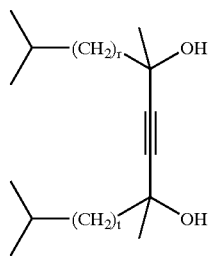

The two base acetylenic diols that were ethoxylated were of the above structure, namely, S-104 (2,4,7,9-tetramethyl-5-decyne-4,7-diol) in which r and t are both 1, i.e., an isobutyl group, and S-124 (2,5,8,11-tetramethyl-6-dodecyne-5,8-diol) in which r and t are both 2, i.e., an isoamyl group.

Following the procedures set forth previously herein, dynamic surface tension (γ) data, foaming data and surfactant efficiency ($pC_{20}$) data were collected for the ethoxylated materials. The surfactant efficiency $pC_{20}$ value is defined as the negative logarithm of the molar concentration of surfactant required to decrease the surface tension of an aqueous solution to 52.1 dyne/cm, that is, 20 dyne/cm below that of pure water when the measurement is performed at 0.1 b/s. This value ($pC_{20}$) is a measure of the efficiency of a surfactant. In general, an increase in $pC_{20}$ value of 1.0 indicates that 10 times less surfactant will be require to observe a given effect, i.e., the higher the value the more efficient the surfactant.

The S-104 ethoxylates were made using the 5.1 mole ethoxylate of 2,4,7,9-tetramethyl-5-decyne-4,7-diol which was prepared by reaction of the starting diol with ethylene oxide in the presence of trimethylamine catalyst at 80° C. using conventional procedures. This 5.1 mole ethoxylate of S-104 was reacted with varying amounts of ethylene oxide using trimethylamine catalyst. A 1000 mL autoclave was charged with the 5.1 mole ethoxylate (210 g, 0.47 moles) which had previously been dried by heating under nitrogen. The reactor was sealed and pressure checked, the air was removed with three nitrogen pressure-vent cycles, and trimethylamine (1.2 g) was added by means of a gas tight syringe. The reactor was pressured to 100 psig (6.7 bar) with nitrogen and heated to 100° C. whereupon ethylene oxide (8.2 g, 9.3 mL, 0.19 moles) was added at a rate of 1 mL/min by means of a syringe pump. At the completion of the addition, the reactor contents were stirred at 100° C. for 4 hours. The reactor was sampled to obtain an aliquot of the 5.5 mole ethoxylate of 2,4,7,9-tetramethyl-5-decyne-4,7-diol. Higher ethoxylates were prepared by adding sufficient ethylene oxide to prepare the 6.5, 7.1, 15, 17, and 25 mole ethoxylates of 2,4,7,9-tetramethyl-5-decyne-4,7-diol. Samples of each ethoxylate were removed from the reactor and characterized by matrix assisted laser-desorption/ionization (MALD/I) analysis.

The surface tension γ and foam data in Table 9 were obtained for 0.1 wt % aqueous solutions of these S-104 ethoxylates. Table 9 also shows the efficiency $pC_{20}$ data.

TABLE 9

| Ex | Additional Moles EO | Total EO | $pC_{20}$ | $\gamma$ 0.1 b/s | $\gamma$ 1 b/s | $\gamma$ 6 b/s | $\gamma$ 15 b/s | $\gamma$ 20 b/s | RM Foam Initial (t to 0) |
|---|---|---|---|---|---|---|---|---|---|
| 54A | 0.4 | 5.5 | 3.90 | 36.6 | 37.7 | 40.0 | 42.8 | 42.3 | 1.5 cm (34s) |
| 54B | 1.4 | 6.5 | 3.78 | 38.2 | 39.4 | 41.9 | 45.2 | 45.2 | 1.5 cm (32s) |
| 54C | 2.0 | 7.1 | 3.84 | 38.8 | 40.1 | 42.6 | 45.7 | 45.3 | 1.5 cm (32s) |
| 54D | 9.9 | 15 | 3.57 | 45.9 | 47.6 | 49.9 | 52.4 | 53.7 | 1.5 cm (2m 27s) |
| 54E | 11.9 | 17 | 3.40 | 46.9 | 48.6 | 50.6 | 52.8 | 54.1 | 1.5 cm (30s) |
| 54F | 19.9 | 25 | 3.34 | 49.8 | 51.6 | 53.3 | 55.2 | 56.3 | 1.3 cm (59s) |

The S-124 ethoxylates were made using the 4 mole ethoxylate of 2,5,8,11-tetramethyl-6-dodecyne-5,8-diol, which is commercially available as Dynol 604 surfactant from Air Products and Chemicals, Inc. This 4 mole ethoxylate of S-124 was reacted with ethylene oxide using trimethylamine catalyst. A 1000 mL autoclave was charged with the 4.0 mole ethoxylate (195 g, 0.44 moles) which had previously been dried by heating under nitrogen. The reactor was sealed and pressure checked, the air was removed with three nitrogen pressure-vent cycles, and trimethylamine (1.2 g) was added by means of a gas tight syringe. The reactor was pressured to 100 psig (6.7 bar) with nitrogen and heated to 100° C. whereupon ethylene oxide (58.31 g, 66.1 mL, 1.32 moles) was added at a rate of 1 mL/min by means of a syringe pump. At the completion of the addition, the reactor contents were stirred at 100° C. for 4 hours. The reactor was sampled to obtain an aliquot of the 7.0 mole ethoxylate of 2,5,8,11-tetramethyl-6-dodecyne-5,8-diol. Higher ethoxylates were prepared by adding sufficient ethylene oxide to prepare the 15, 17, and 25 mole ethoxylates of 2,5,8,11-tetramethyl-6-dodecyne-5,8-diol. Samples of each ethoxylate were removed from the reactor and characterized by matrix assisted laser-desorption/ionization (MALD/I) analysis.

The surface tension $\gamma$ and foam data in Table 10 were obtained for 0.1 wt % aqueous solutions of these S-124 ethoxylates. Table 10 also shows the efficiency $pC_{20}$ data.

TABLE 10

| Ex | Additional Moles EO | Total EO | $pC_{20}$ | $\gamma$ 0.1 b/s | $\gamma$ 1 b/s | $\gamma$ 6 b/s | $\gamma$ 15 b/s | $\gamma$ 20 b/s | RM Foam Initial (t to 0) |
|---|---|---|---|---|---|---|---|---|---|
| 54G | 3.0 | 7.0 | 4.45 | 27.3 | 27.9 | 30.1 | 36.3 | 35.2 | 4.9 cm (>300 s) |
| 54H | 11.0 | 15.0 | 4.28 | 33.6 | 38.4 | 42.3 | 45.8 | 42.7 | 3.0 cm (>300 s) |
| 54J | 13.0 | 17.0 | 4.10 | 36.3 | 40.6 | 44.0 | 47.5 | 46.3 | 3.0 cm (>300 s) |
| 54K | 15.0 | 25.0 | 3.96 | 42.5 | 45.5 | 48.1 | 50.9 | 52.5 | 2.1 cm (>300 s) |

EXAMPLE 55

Table 11 presents additional surface tension ($\gamma$), foam and efficiency ($pC_{20}$) data which had been generated for the S-104 and S-124 ethoxylate/propoxylates shown in Table 7.

TABLE 11

| Ex | Base Diol | R or B | EO Moles | PO Moles | EO & PO | $pC_{20}$ | $\gamma$ 0.1 b/s | $\gamma$ 1 b/s | $\gamma$ 6 b/s | $\gamma$ 15 b/s | $\gamma$ 20 b/s | RM Foam (cm) Initial (t to 0) |
|---|---|---|---|---|---|---|---|---|---|---|---|---|
| 39 | S-104 | R | 5 | 10 | 15 | 4.50 | 33.4 | 33.7 | 39.9 | 46.1 | 48.2 | 0.5 (1s) |
| 40 | S-104 | B | 5 | 10 | 15 | 4.58 | 34.3 | 37.2 | 40.5 | 43.1 | 45.7 | 0.5 (10s) |
| 41 | S-104 | R | 15 | 2 | 17 | 4.20 | 32.3 | 36.0 | 43.8 | 49.0 | 50.7 | 4.5 (>300s) |
| 42 | S-104 | B | 15 | 2 | 17 | 5.04 | 30.4 | 36.8 | 42.9 | 47.5 | 49.5 | 5.3 (>300s) |
| 43 | S-104 | R | 15 | 10 | 25 | 4.42 | 31.0 | 33.8 | 44.5 | 48.3 | 52.8 | 2.8 (>300s) |
| 44 | S-104 | B | 15 | 10 | 25 | 4.35 | 30.7 | 35.5 | 45.6 | 52.0 | 54.9 | 4.0 (>300s) |
| 45 | S-124 | R | 5 | 2 | 7 | 4.39 | 27.2 | 28.2 | 33.5 | 42.5 | 45.4 | 2.4 cm (0.2 cm) |
| 46 | S-124 | B | 5 | 2 | 7 | 4.42 | 27.4 | 28.5 | 32.5 | 37.7 | 37.2 | 3.0 cm (0.3 cm) |
| 47 | S-124 | R | 5 | 10 | 15 | 4.57 | 30.8 | 31.8 | 40.8 | 52.5 | 55.1 | 1.8 cm (>300s) |
| 48 | S-124 | B | 5 | 10 | 15 | 4.56 | 32.1 | 33.4 | 40.3 | 51.6 | 55.4 | 1.4 cm (>300 s) |
| 49 | S-124 | R | 15 | 2 | 17 | 4.36 | 28.0 | 30.5 | 40.8 | 47.5 | 50.2 | 2.6 cm (>300 s) |

TABLE 11-continued

| Ex | Base Diol | R or B | EO Moles | PO Moles | EO & PO | $pC_{20}$ | $\gamma$ 0.1 b/s | $\gamma$ 1 b/s | $\gamma$ 6 b/s | $\gamma$ 15 b/s | $\gamma$ 20 b/s | RM Foam (cm) Initial (t to 0) |
|----|-----------|--------|----------|----------|---------|-----------|-----------------|----------------|----------------|-----------------|-----------------|-------------------------------|
| 50 | S-124 | B | 15 | 2 | 17 | 4.17 | 28.6 | 31.1 | 42.5 | 47.4 | 50.0 | 2.5 cm (>300 s) |
| 51 | S-124 | R | 15 | 10 | 25 | 4.58 | 30.1 | 32.8 | 43.2 | 46.7 | 45.5 | 2.0 cm (>300 s) |
| 52 | S-124 | B | 15 | 10 | 25 | 4.55 | 29.9 | 33.7 | 41.4 | 46.9 | 48.8 | 4.8 cm (>300 s) |

EXAMPLE 56

(a) A commercial photoresist based on a novolac-type cresol/formaldehyde resin and a diazonaphthoquinone (DNQ) photosensitive agent (SPR510 A, Shipley) was coated on a 4 inch silicon wafer to a thickness of approximately 1 micron following the manufacturer's instructions. Different areas of the resist were then exposed to UV radiation centered at 365 nm (mercury i-line) at various levels of intensity by positioning the wafer under an aperture opening and operating a shutter. The resulting exposed wafer was developed (60 Seconds) in a puddle of 0.262 M tetramethylammonium hydroxide (TMAH) containing sufficient PO terminated acetylenic alcohol derivative (Example 4 adduct) to lower the surface tension of the developer to 42 dynes/cm. The various portions of the wafer were then examined for film thickness using a Filmetrics F20 Thin-Film Measuring System (San Diego, Calif.) and the results were compared to the film thicknesses before exposure and developing. The Normalized Film Thickness is a dimensionless ratio and was calculated by dividing the pre-exposure film thickness by the post-development film thickness. The results are shown in Table 12, Example 56(a)

(b) Similarly, the photoresist was exposed through a variable transmission filter (obtained from Opto-Line Associates, Wilmington Mass.) which consisted of a circular area on a quartz plate broken up into wedges of varying transmission levels. The results are shown in Table 12, Example 56(b). These data show outstanding selectivity of the developer solution for dissolution of the highly exposed resist vs. mildly exposed resist.

(c) Another commercially available photoresist (OCG 825 20 cS, Olin Corporation) was used to coat a 4 inch silicon wafer with a film thickness of approximately 1 micron. This resist is designed to be much more soluble in developer solutions and was used with 0.131 M TMAH. Table 12, Example 56(c) shows data for the dissolution of exposed resist with 0.131 M TMAH containing 0.00625 wt % (62.5 ppm) of the adduct of Example 4. Again, a development time of 60 seconds was used. The data show outstanding selectivity, even with the highly sensitive photoresist formulation.

TABLE 12

| Example 56(a) | | Example 56(b) | | Example 56(c) | |
|---|---|---|---|---|---|
| Dose (mJ/cm$^2$) | Normalized Film Thickness | Dose (mJ/cm$^2$) | Normalized Film Thickness | Dose (mJ/cm$^2$) | Normalized Film Thickness |
| 19.42 | 0.98 | 2.66 | 0.998 | 0.81 | 0.992 |
| 24.28 | 0.96 | 2.81 | 0.997 | 0.86 | 0.993 |
| 30.35 | 0.83 | 3.26 | 0.996 | 0.99 | 0.990 |
| 38.85 | 0.61 | 9.99 | 0.994 | 3.05 | 0.983 |
| 48.56 | 0.40 | 11.92 | 0.994 | 3.64 | 0.979 |
| 60.70 | 0.20 | 17.47 | 0.988 | 5.34 | 0.962 |
| 95.91 | 0.00 | 25.39 | 0.972 | 7.75 | 0.933 |
| 121.40 | 0.00 | 36.26 | 0.707 | 11.1 | 0.854 |
| 152.96 | 0.00 | 52.92 | 0.204 | 16.2 | 0.697 |
| 191.81 | 0.00 | 66.39 | 0.096 | 20.3 | 0.561 |
| 242.80 | 0.00 | 92.44 | 0.001 | 28.2 | 0.345 |
| 304.71 | 0.00 | 117.9 | 0.000 | 36.0 | 0.196 |
| | | 152.83 | 0.000 | 46.7 | 0.025 |
| | | 196.71 | 0.000 | 60.1 | 0.000 |
| | | 221.8 | 0.000 | 67.8 | 0.000 |

EXAMPLE 57

Comparisons were made of the effectiveness of the Example 4 adduct with ethoxylated adducts of the prior art in reducing surface tension in 0.262 M TMAH solutions. As can be seen from the data of Table 13, significantly higher amounts of the prior art ethoxylated adducts were required to obtain surface tensions comparable to the adduct of Example 4 which was both ethoxylated and propoxylated, containing 5.1 moles of EO and 2.0 moles of PO per molecule. The prior art adducts were those described in Table 5 for Comparative Examples 29, 30 and 31 and contained 3.5, 5.1 and 10 moles, respectively, of EO per molecule.

TABLE 13

| Wetting Agent | Conc (ppm) | Surface Tension (dyne/cm) |
|---|---|---|
| Ex 29 (EO 3.5 mol) | 150 | 41.9 |
| Ex 30 (EO 5.1 mol) | 150 | 42.7 |
| Ex 31 (EO 10 mol) | 500 | 41.3 |
| Ex 4 (5.1 EO, 2.0 PO) | 125 | 41.9 |

EXAMPLE 58

Foam tests were made in TMAH developer solutions formulated with the EO/PO adduct of Example 4 and the EO adduct of Example 31 as surfactants and with six commercial developer solutions containing surfactants. Data were collected utilizing a foam generating apparatus whereby nitrogen gas was passed through a frit and bubbled through 100 mL of the solutions at 50 mL/min. Except for the commercial developer solutions which were used as received, all solutions contained 2.4 wt % TMAH in water with enough surfactant to lower surface tension to 41–43 dyne/cm. The results are given in Table 14.

TABLE 14

| | | | Foam Volume (mL) | | | | | |
|---|---|---|---|---|---|---|---|---|
| Time (min) | Ex. 4 | Ex. 31 | OCG 934 3:2[a] | MF-702[b] | MF-319[b] | 10R5[c] | 17R2[c] | L31[c] |
| 0 | 0.0 | 0.0 | 0.0 | 0.0 | 0.0 | 0.0 | 0.0 | 0.0 |
| 1 | 7.8 | 7.5 | 15.6 | 39.5 | 51.1 | 20.5 | 15.4 | 20.2 |
| 2 | 7.2 | 7.5 | 17.2 | 72.6 | 91.4 | 21.1 | 16.2 | 20.5 |
| 3 | 7.1 | 7.5 | 24.2 | 107.4 | 135.3 | 22.6 | 16.7 | 21.4 |
| 4 | 7.2 | 7.5 | 22.9 | 156.4 | 176.8 | 21.7 | 16.9 | 21.1 |
| 5 | 7.2 | 7.5 | 22.3 | 172.8 | 237.8 | 22.3 | 16.5 | 21.4 |
| 6 | 7.3 | 7.5 | 22.0 | 236.2 | 275.1 | 22.6 | 16.9 | 22.3 |
| 7 | 7.1 | 7.5 | 25.8 | 287.0 | 321.3 | 22.6 | 16.9 | 21.7 |
| 8 | 7.1 | 7.5 | 25.8 | 307.6 | 372.6 | 22.0 | 17.4 | 22.0 |
| 9 | 7.1 | 7.5 | 25.5 | 326.9 | 416.7 | 22.9 | 17.2 | 22.0 |
| 10 | 7.5 | 7.5 | 26.2 | 301.3 | 460.6 | 22.6 | 17.4 | 22.3 |
| 11 | 7.7 | 7.5 | 26.5 | 340.2 | 502.0 | 22.3 | 17.6 | 22.6 |
| 12 | 7.9 | 7.5 | 26.9 | 404.8 | 544.9 | 22.0 | 17.4 | 22.3 |
| 13 | 7.8 | 7.5 | 26.9 | 438.6 | 594.7 | 22.6 | 17.6 | 22.6 |
| 14 | 7.9 | 7.5 | 26.9 | 488.6 | 647.5 | 22.0 | 17.6 | 22.3 |
| 15 | 7.8 | 7.5 | 27.3 | 514.9 | 681.1 | 22.3 | 18.1 | 22.6 |

[a]Commercial developer solution from Olin (now Arch Chemical)
[b]Commercial developer marketed under Microposist ® trademark by Shipley
[c]Commercial surfactant marketed under Pluronic ® trademark by BASF The above data show that TMAH developer solutions containing the EO/PO adduct surfactant of Example 4 developed considerably less foam than the commercial developer solutions containing other types of surfactant. Although the foam volumes for the developer solution containing the Example 31 EO adduct were close to those for the developer containing the EO/PO adduct of Example 4, the data of Table 13 show that considerably less EO/PO adduct surfactant was required to achieve comparable reduction in surface tension.

EXAMPLE 59

Further runs were made to examine foaming tendencies of photoresist developers containing the surfactants of Example 4, 29 and 30. These measurements were made using the Ross-Miles technique and were determined in 0.262 N TMAH solutions. The results are given in Table 15.

TABLE 15

| Wetting Agent | Conc (ppm) | RM Foam, initial (t to 0) |
|---|---|---|
| Ex 29-3.5 EO adduct | 150 | 1.7 cm (15 s) |
| Ex 30-5.1 EO adduct | 150 | 2.7 cm (27 s) |
| Ex 4-EO/PO adduct | 125 | 1.5 cm (6 s) |

The above data in Table 15 show that low foam is achieved with the ethoxylated-propoxylated adduct. It is quite surprising that partial propoxylation of acetylenic alcohols which are also ethoxylated increases the ability of these adducts to reduce both surface tension and foaming tendency in TMAH developer solutions while maintaining good contrast for photoresist developing applications. These goals are achieved while lowering the level of acetylenic alcohol derivative required for a desired surface tension reduction.

In sum, the ability of a surfactant to reduce surface tension under both equilibrium and dynamic conditions is of great importance in the performance of waterbased coatings, inks, adhesives, fountain solutions, agricultural compositions, and photoresist developers. Low dynamic surface tension results in enhanced wetting and spreading under the dynamic conditions of application, resulting in more efficient use of the compositions and fewer defects. Foam control is also an important attribute in many applications, but particularly so in photoresist developer, or electronics cleaning compositions.

The family of surfactants disclosed in this invention provides an ability to control foam while providing excellent dynamic surface tension reduction. They will therefore have utility in applications such as coatings, inks, adhesives, fountain solutions, agricultural compositions, soaps and detergents. Their use in photoresist developer/electronics cleaning compositions is especially advantageous.

STATEMENT OF INDUSTRIAL APPLICATION

The invention provides compositions suitable for reducing the equilibrium and dynamic surface tension in waterbased coating, ink, fountain solution, agricultural, and photoresist developer/electronics cleaning compositions.

We claim:

1. An aqueous photoresist developer composition containing as a surfactant an acetylenic diol ethylene oxide/propylene oxide adduct represented by the general structure:

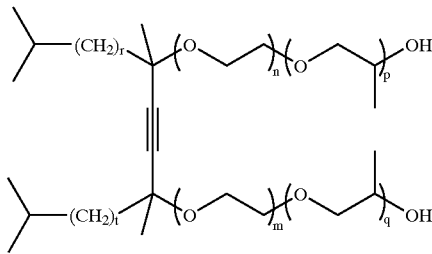

where r and t are 1 or 2, (n+m) is 1.3 to 30 and (p+q) is 1 to 10, and the ethylene oxide units (n and m) and the propylene oxide units (p and q) being distributed along the alkylene oxide chain in blocks or randomly.

2. The composition of claim 1 in which the ethylene oxide and propylene oxide units are distributed along the alkylene oxide chain in blocks.

3. The composition of claim 2 in which the ethylene oxide/propylene oxide adduct is capped with the propylene oxide units.

4. The composition of claim 3 in which (n+m) is 1.3 to 15.

5. The composition of claim 3 in which (n+m) is 1.3 to 10 and (p+q) is 1 to 3.

6. The composition of claim 3 in which the acetylenic diol moiety of the acetylenic diol ethylene oxide/propylene oxide adduct is derived from 2,4,7,9-tetramethyl-5-decyne-4,7-diol.

7. The composition of claim 3 in which the acetylenic diol moiety of the acetylenic diol ethylene oxide/propylene oxide adduct is derived from 2,5,8,11-tetramethyl-6-dodecyne-5,8-diol.

8. The composition of claim 6 in which (n+m) is 1.3 to 10 and (p+q) is 1 to 3.

9. The composition of claim 7 in which (n+m) is 1.3 to 10 and (p+q) is 1 to 3.

10. The composition of claim 8 in which (p+q) is 2.

11. The composition of claim 9 in which (p+q) is 2.

12. The composition of claim 10 in which the acetylenic diol ethylene oxide/propylene oxide adduct is the 5 mole ethoxylate/2 mole propoxylate adduct of 2,4,7,9-tetramethyl-5-decyne-4,7-diol.

13. The composition of claim 1 containing tetramethylammonium hydroxide.

14. In a process for developing a photoresist after exposure to radiation by applying to the photoresist surface a developer solution containing a surface tension lowering amount of a surfactant, the improvement which comprises using as the surfactant an acetylenic diol ethylene oxide/propylene oxide adduct having a molecular structure represented by the general formula:

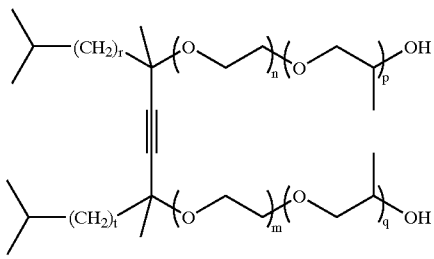

where r and t are 1 or 2, (n+m) is 1.3 to 30 and (p+q) is 1 to 10, the units of ethylene oxide (n and m) and propylene oxide (p and q) being distributed along the alkylene oxide chain in blocks with the propylene oxide units capping the chain.

15. The process of claim 14 in which the developer solution contains tetramethylammonium hydroxide.

16. The process of claim 14 in which (n+m) is 1.3 to 10 and (p+q) is 1 to 3.

17. The process of claim 16 in which the acetylenic diol moiety of the acetylenic diol ethylene oxide/propylene oxide adduct is derived from 2,4,7,9-tetramethyl-5-decyne-4,7-diol.

18. The process of claim 16 in which the acetylenic diol moiety of the acetylenic diol ethylene oxide/propylene oxide adduct is derived from 2,5,8,11-tetramethyl-6-dodecyne-5,8-diol.

19. The process of claim 16 in which the developer solution contains tetramethylammonium hydroxide.

20. An aqueous electronics cleaning composition comprising in water the following components 0.1 to 3 wt % tetramethylammonium hydroxide, 0 to 4 wt % phenolic compound; and 10 to 10,000 ppm acetylenic diol ethylene oxide/propylene oxide adduct, the acetylenic diol ethylene oxide/propylene oxide adduct having a molecular structure represented by the general formula:

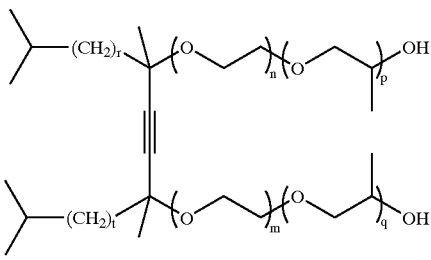

where r and t are 1 or 2, (n+m) is 1.3 to 10 and (p+q) is 2, the units of ethylene oxide (n and m) and propylene oxide (p and q) being distributed in blocks and capped with the propylene oxide units.

* * * * *